United States Patent [19]

Miller

[11] 4,137,761
[45] Feb. 6, 1979

[54] TILTING TABLE INITIAL TACK TEST APPARATUS FOR ADHESIVE BONDS

[75] Inventor: Donald Miller, Rockaway, N.J.

[73] Assignee: The United States of America as represented by the Secretary of the Army, Washington, D.C.

[21] Appl. No.: 841,188

[22] Filed: Oct. 11, 1977

[51] Int. Cl.² ............................................. G01N 19/04
[52] U.S. Cl. .................................... 73/150 A; 108/6
[58] Field of Search ......................... 73/150 A, 150 R; 248/441 B; 108/6

[56] References Cited

U.S. PATENT DOCUMENTS

| 1,114,677 | 10/1914 | Brooks | 108/6 |
| 3,303,697 | 2/1967 | Schroeder | 73/150 A X |
| 3,756,166 | 9/1973 | Piretti | 108/6 |

Primary Examiner—Charles Gorenstein
Attorney, Agent, or Firm—Nathan Edelberg; Harold H. Card, Jr.; A. Victor Erkkila

[57] ABSTRACT

The adhesive bond test apparatus comprises: a U-shaped bracket of aluminum, supported on a table; a tiltable rectangular panel of aluminum pivotally mounted in the U of the bracket for tilting between a horizontal and a vertical position; a sheet adherend made of two Kraft paper layers bonded together with asphalt, attached to one surface of the panel; a plurality of elongated strips adherends each having a specified weight attached to one end, and the other end bonded over a given small area to a portion of the sheet adherend that will be up in vertical position, wherein the weight applies a constant gravity load to the bond during the test. Both shear and a pull tests are disclosed.

9 Claims, 3 Drawing Figures

TILTING TABLE INITIAL TACK TEST APPARATUS FOR ADHESIVE BONDS

GOVERNMENT INTEREST

The invention described herein may be manufactured, used and licensed by or for the Government for government purposes without the payment to me of any royalty thereon.

BACKGROUND AND SUMMARY OF THE INVENTION

The present invention relates to apparatus for making initial tack tests for various adhesives. The apparatus prescribed by the U.S. Army for making such initial tack tests is described in paragraph 4.4.4 of Federal Specification MMM260A, substantially as follows:

"4.4.4 Initial Tack. Separate tests shall be made using class H-4 and L-2 materials at a temperature of 73° ± 2° F., and 50 ± 5 percent relative humidity. By means of suitable adhesive, a specimen of the barrier materials shall be securely bonded to one end of (each of) two smooth, clean steel cylinders, each having a diameter of 1 ± 0.009 inch, weighing 12 ounces ± 0.010 ounce, and approximately 3 inches long. The ends of the cylinders shall be clean, and flat squared perpendicular to their lengths. The bonded barrier material applied as above shall be trimmed carefully so that a disc is formed closely conforming to the one inch diameter of the cylinder. With each cylinder in an upright position, a film of the adhesive covered by this specification shall be applied in the thickness recommended by the manufacturer to each barrier material disc and allowed to dry for 30 seconds (except that class 3 — hot melt adhesives shall be subjected to the next operation within 10 seconds of adhesive film coating discs), the time being determined from the beginning of the adhesive application. A duplicate cylinder (with similar adhered discs) shall be placed on top of the first, so that the cylinders are aligned and the barrier material discs are adjacent, with only the specification adhesive between. The crepe direction of the barrier material discs shall be in the same direction and care taken in placing the top cylinder on the lower cylinder not to apply any pressure other than the weight of the upper cylinder. Specimens having discs of H-4 barrier material shall have an additional 12 ounce load applied on the upper cylinder. Sixty seconds after applying the cylinders together (80 seconds for class 3-hot melt adhesives), each assembly shall be raised by lifting the upper bonded cylinder until the bottom cylinder is free of the supporting surface. A total of 10 assemblies (20 bonded cylinders) using each of the above barrier materials (in disc form) shall be so tested. A minimum of 7 of the 10 specimens of each variety shall be so raised without separation of the adhesive bond between the discs in order to comply with the requirement for initial tack."

A major criticism of paragraph 4.4.4 is that the test results are more a measure of skill of the technician in specimen preparation than the initial tack of the adhesive being measured. The diameter of the test discs result in large variations in the effective bonding area. There is often a great deal of scatter on repeated tests with the same material.

An object of the present invention is to provide an entirely different, and improved, apparatus and method for making initial tack tests for adhesive bonds.

In accordance with the invention, the improved apparatus comprises a U-shaped bracket adapted to be supported in a horizontal plane, e.g. on a table; a tiltable elongated panel pivotally supported within the U for tilting from a horizontal to a vertical position; a first adherend affixed to the panel; at least one elongated second adherend adhesively bonded at least at one end to a portion of the first adherend that is up in the vertical position; and a weight affixed to the second adherend to apply a constant gravity load to the adhesive bond in the vertical position. Preferably, the first adherend is a sheet, covering the panel, to the upper edge of which the upper ends of several strip adherends are adhesively bonded, with a seperate weight on each strip adherend. The strip adherends may be either fold-bonded to the sheet adherend for a peel test, or flat-bonded for a shear test. Each adherend is preferably made of two layers of Kraft paper bonded by a thin layer of asphalt. An elongated block may be attached to the bracket legs to stop the panel in its vertical position. The invention provides an apparatus that can be used with great reliability by technicians with little or no training.

DETAILED DESCRIPTION OF THE INVENTION

Figure 1:
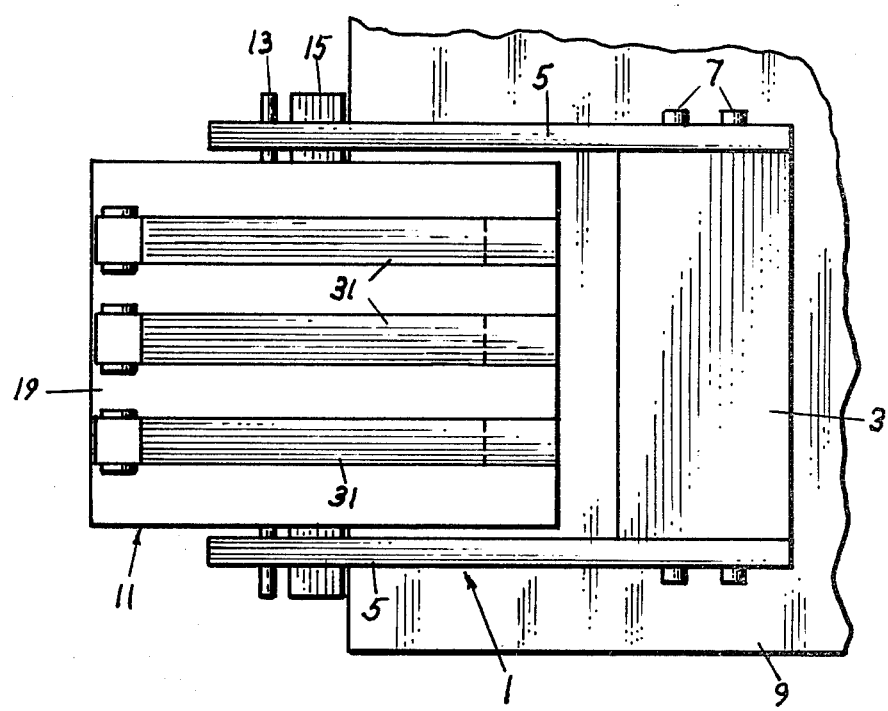
FIG. 1 is a top plan view of a test apparatus embodying the invention, including a tiltable panel in a horizontal position.
Figures 2, 3:
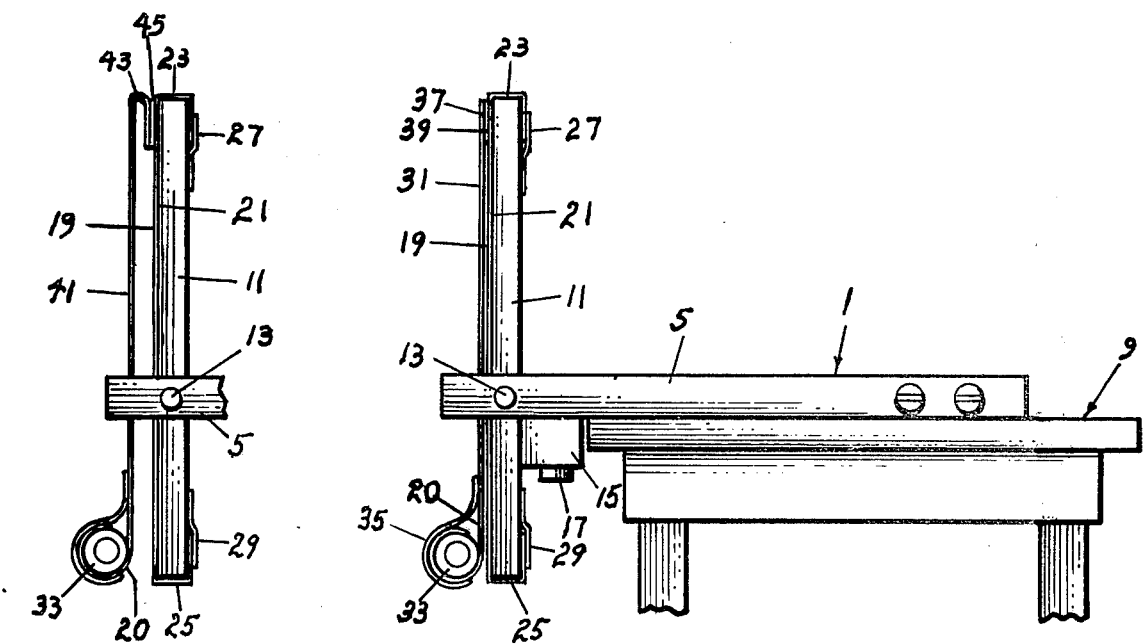
FIG. 2 is a side view of the apparatus of FIG. 1, with the tiltable panel in a vertical position.
FIG. 3 is a similar side view of a modification of the panel of FIG. 2.

A preferred embodiment of the invention is illustrated in FIGS. 1 and 2. The test apparatus comprises a U-shaped aluminum bracket 1 made up of a transverse base 3 to which two parralled legs 5 are attached, by steel screws 7. The bracket is supported by resting the major portion thereof on a horizontal support, such as a table 9. A tiltable aluminum test panel 11, of flat rectangular shape, is pivotally connected, by steel pins 13, to the bracket legs 5 for tilting movement between a horizontal position, shown in FIG. 1, and a vertical position, shown in FIG. 2. An elongated block 15, attached by steel screws 17 the legs 5, serves as a stop to limit the vertical tilting of the panel 11 to 90°.

In preparation for the initial tack tests, a first adherend 19, in the form of a sheet, e.g. made up of two layers of Kraft paper bonded together by a layer of asphalt, is affixed to the front surface 21 of panel 11, by folding the upper and lower edges 23 and 25 over the edges of the panel and attaching them to the panel by adhesive tapes 27 and 29 (FIG. 2), and the panel is placed in its horizontal position, shown in FIG. 1. One or more elongations strip adherends 31, which may be cut from a sheet of the same material as the sheet adherend 19, are prepared for adhesive bonding to the first adherends 19 by attaching a specified weight 33 to one end of each strip adherend 19 around the weight and fixing it to the strip by an adhesive tape 35. The width of the strip adherends 19 may, for example, be 1 inch.

The strip adherends 19, with the weights 33 attached to one end 20, are placed on the sheet adherend 19 and the other ends 37 thereof are separately bonded at 39, over a specified area, to a portion of the sheet adherend 19, adjacent to the edge 23. The thickness of this bond 39 is shown greatly exaggerated in FIG. 2. The length of the bond 39 parallel to the strip 31 may be 1.5 inches. In making the bond 39, drops of the adhesive being tested are placed on the center of the designated joint area of the sheet adherend 19. The adhesive is a rubber cement which sets by giving off solvents. The joint portion of the strip adherened 31 is wiped into the drops of adhesive until the adhesive is spread over the entire joint area of both adherends, and these surfaces are separated and allowed to dry for 30 seconds. The adhesive-coated surfaces are then joined, and a light load may be placed on the top of the bond area and held for 60 seconds. The light load is then removed (if used) and the table is tilted to a vertical position in which the gravity loads of the weight 33 are applied to the bonds 39 through the strip adherends 31. The maximum allowable time for tilting 90° is 6 seconds. The bond shown in FIGS. 1 and 2, where the flat upper end of each strip adherend 31 is bonded to the sheet adherend 19 without any folding, may be called a "shear bond", in which the bond strength is tested predominatly only in shear. In this case, the bond is tested by determining the weight that is required to induce failure, and/or the time to failure under a given weight, for a given adhesive, in a given bond area. Thus, the variables that may be involved in the test include:

1. The adherends and adhesives used;
2. Variability of the tilt angle (0 to 90°);
3. The size and shape of the joint area;
4. The thickness of the adhesive bond; and
5. The size of the weight.

FIG. 3 shows a modification of FIGS. 1 and 2, wherein the adhesive bond is "peel" tested, instead of being "shear" tested. The apparatus is essentially the same as that of FIG. 1, except for the manner of bonding the upper edge of the strip adherends to the sheet adherend, and the same numerals have been applied to identical elements in FIGS. 2 and 3. FIG. 3 shows a strip adherend 41, which is slightly longer than those in FIGS. 1 and 2, and may be made of the same material, that is folded back on itself at 43 before being bonded at 45 to the sheet adherend 19. The bond 45 may be made in the same manner as the bond 39 in FIG. 2. However, since the load provided by the weight 33 is applied to the top edge of the bond (45), instead of the bottom edge as in FIG. 2, the bond opens at the top first under test, and hence, the bond fails in the direction from top to bottom. Thus, the strip adherend 41 "peels" away from the sheet adherend 19 when the bond fails. Peel tests, which were made with the arrangement shown in FIG. 3 prior to the shear tests that were made with the arrangement shown in FIG. 2, showed that the rate of peeling was sometimes too rapid to easily measure. Also, using each test on given sample sizes there were greater numbers of failures in peel test samples than in shear test samples. This led to the adoption of the shear test rather than the peel test as the preferred test. However, the peel test is considered satisfactory for stronger adhesive bonds which do not fail, or which peel at a lower rate during failure.

The foregoing disclosure and drawings are merely illustrative of the principles of this invention and are not to be interpreted in a limiting sense. I wish it to be understood that I do not desire to be limited to the exact details of construction shown and described, because obvious modifications will occur to a person skilled in the art.

I claim:
1. Apparatus for testing adhesive bonds comprising: a bracket including a transverse base and two side legs forming a U-shaped opening, and adapted to be supported substantially in a horizontal plane; a tiltable panel positioned within said opening and pivotally connected at points intermediate the ends thereof to the outer ends of said legs for tilting from a horizontal position to a vertical position; stop means for limiting the tilting of said panel, comprising an elongated block of rectangular cross section attached to the undersides of said bracket legs and abutting said panel in each of the horizontal and vertical positions thereof; a first adherend affixed to said panel; at least one elongated second adherend adhesively bonded at least at one end to a portion of said first adherend that is up in said vertical position; and a weight affixed to said second adherend, for applying a constant gravity load to the adhesive bond between said adherends, in said vertical position.

2. Apparatus as in claim 1, wherein: said first adherend is a sheet covering the top surface of said panel; and said second adherend is a narrow elongated strip overlying a narrow elongated region of said sheet.

3. Apparatus as in claim 2, wherein said second adherend includes a plurality of strip adherends separately bonded to said sheet adherend, with a separate weight affixed to each strip adherend.

4. Apparatus as in claim 1, wherein each of said adherends is made of two layers of Kraft paper bonded by a thin layer of asphalt.

5. Method of testing adhesive bonds comprising: supporting a bracket, including a transverse base and two side legs forming a U-shaped opening, substantially in a horizontal plane; positioning an elongated panel within said opening, initially coplanar with said bracket, and pivotally connecting said panel to said legs for tilting between horizontal and vertical positions: affixing a first adherend to said panel; positioning at least one second adherend on said first adherend; forming an adhesive bond between at least a portion of said second adherend and a portion of said first adherend that will be up in said vertical position of said panel; attaching a weight to said second adherend; tilting said panel to said vertical position; and measuring the time required to rupture said adhesive bond.

6. The method of claim 5, wherein; said first adherend is a sheet covering the top surface of said panel; and said second adherend is an elongated strip overlying a narrow region of said sheet.

7. The method of claim 6, wherein said strip is bonded to said sheet in a predetermined small end portion only.

8. The method of claim 7, wherein said weight is effectively attached to said strip at the lower edge of said bond; whereby said bond is shear tested.

9. The method of claim 6, wherein: said weight is effectively attached to said strip at the upper edge of said bond; whereby said bond is peel tested.

* * * * *